(12) United States Patent
Kudo (10) Patent No.: US 7,756,242 B2
(45) Date of Patent: Jul. 13, 2010

(54) X-RAY CT APPARATUS AND SCAN CONTROL METHOD

(75) Inventor: Masayuki Kudo, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 12/174,437

(22) Filed: Jul. 16, 2008

(65) Prior Publication Data

US 2009/0022268 A1 Jan. 22, 2009

(30) Foreign Application Priority Data

Jul. 18, 2007 (JP) ............... 2007-187236

(51) Int. Cl.
G01N 23/083 (2006.01)
A61B 6/04 (2006.01)

(52) U.S. Cl. .................. 378/15; 378/20; 378/208; 378/209

(58) Field of Classification Search .............. 378/4–20, 378/193–195, 204, 208, 209
See application file for complete search history.

(56) References Cited

U.S. PATENT DOCUMENTS

| | | | |
|---|---|---|---|
| 5,218,623 A | 6/1993 | Toki et al. |
| 5,386,446 A | 1/1995 | Fujimoto et al. |
| 5,696,807 A | 12/1997 | Hsieh |
| 6,023,494 A | 2/2000 | Senzig et al. |
| 6,275,562 B1 | 8/2001 | He et al. |
| 6,366,638 B1 | 4/2002 | Hsieh et al. |
| 6,385,278 B1 | 5/2002 | Hsieh |
| 6,418,183 B1 | 7/2002 | Fox et al. |
| 6,587,537 B1 | 7/2003 | Hsieh |
| 6,775,352 B2 | 8/2004 | Toth et al. |
| 6,901,129 B2 | 5/2005 | Tachizaki et al. |
| 7,050,532 B2 | 5/2006 | Gohno |
| 7,079,618 B2 | 7/2006 | Tsuyuki |
| 7,103,139 B2 | 9/2006 | Nagaoka et al. |
| 7,173,997 B2 | 2/2007 | Hagiwara |
| 2002/0037068 A1* | 3/2002 | Oikawa ............... 378/15 |
| 2002/0191737 A1 | 12/2002 | Tanigawa |
| 2003/0123603 A1 | 7/2003 | Suzuki |
| 2004/0114706 A1* | 6/2004 | Ikeda et al. ........... 378/4 |

(Continued)

FOREIGN PATENT DOCUMENTS

JP 2006-320523 11/2006

*Primary Examiner*—Edward J Glick
*Assistant Examiner*—Anastasia Midkiff
(74) *Attorney, Agent, or Firm*—Armstrong Teasdale LLP (57) ABSTRACT

The present invention is directed to realize an X-ray CT apparatus and a scan control method of performing contrast imaging by a helical shuttle scan with a smaller exposure amount. An X-ray CT apparatus for performing contrast imaging by repeating a reciprocating helical scan on a region in a subject repeats the helical shuttle scan (solid-line arrow) including, in shuttle (broken-line arrow) of a helical shuttle scan using an X-ray of a first X-ray dose, a helical scan using an X-ray of a second X-ray dose higher than the first X-ray dose. The start timing of the helical scan using the X-ray of the second X-ray dose is determined on the basis of a change in the CT number of a region of interest of an image captured by a helical scan using the X-ray of the first X-ray dose.

16 Claims, 10 Drawing Sheets

U.S. PATENT DOCUMENTS

| | | |
|---|---|---|
| 2005/0157840 A1 | 7/2005 | Gohno et al. |
| 2006/0050840 A1* | 3/2006 | Ikeda et al. .................... 378/8 |
| 2006/0262896 A1* | 11/2006 | Nishide et al. ................ 378/15 |
| 2007/0286332 A1* | 12/2007 | Gohno et al. ................ 378/15 |
| 2008/0031407 A1* | 2/2008 | Satta et al. .................... 378/15 |
| 2008/0144764 A1* | 6/2008 | Nishide et al. ................. 378/5 |
| 2008/0152076 A1* | 6/2008 | Hagiwara .................... 378/20 |
| 2008/0260092 A1* | 10/2008 | Imai et al. ..................... 378/5 |
| 2009/0022263 A1* | 1/2009 | Imai .............................. 378/5 |

* cited by examiner

X-RAY CT APPARATUS AND SCAN CONTROL METHOD

CROSS REFERENCE TO RELATED APPLICATIONS

This application claims the benefit of Japanese Patent Application No. 2007-187236 filed Jul. 18, 2007, which is hereby incorporated by reference in its entirety.

BACKGROUND OF THE INVENTION

The subject matter disclosed herein relates to an X-ray CT (Computed Tomography) apparatus and a scan control method and, more particularly, to an X-ray CT apparatus for performing contrast imaging by repeating a helical shuttle scan on the same region in a subject and to a scan control method for such an X-ray CT apparatus.

At the time of capturing a plurality of slice images continuous in the body axis direction, a helical scan is performed. The helical scan can be performed in a reciprocating manner. Such a scan is called a shuttle mode helical scan or a helical shuttle scan (refer to, for example, Japanese Unexamined Patent Application Publication No. 2006-320523 (paragraphs 0039, 0040, 0064, and 0065 and FIGS. 3 and 28)).

BRIEF DESCRIPTION OF THE INVENTION

For example, at the time of capturing slice images of an artery phase, a portal phase, a venous phase, and the like of an entire liver, a helical shuttle scan is performed continuously for predetermined time with a uniform X-ray dose on the abdomen of the subject to which a contrast agent is injected. Consequently, an exposure amount of the subject becomes large.

The embodiments described herein provide an X-ray CT apparatus and a scan control method for performing contrast imaging by a helical shuttle scan with a reduced exposure amount.

According to a first aspect of the, there is provided an X-ray CT apparatus for performing contrast imaging by repetition of a helical shuttle scan on the same region in a subject, including scan device for repeating a helical shuttle scan including a helical scan using an X-ray of a first X-ray dose and a helical scan using an X-ray of a second X-ray dose higher than the first X-ray dose.

According to a second aspect, in the X-ray CT apparatus according to the first aspect, the scan device determines a start timing of the helical scan using the X-ray of the second X-ray dose on the basis of a change in a CT number of a region of interest in an image captured by the helical scan using the X-ray of the first X-ray dose.

According to a third aspect, in the X-ray CT apparatus according to the first or second aspect, the scan device sets the first X-ray dose and the second X-ray dose for each of one way of paths of the helical shuttle scan and repeats the helical shuttle scan.

According to a fourth aspect, in the X-ray CT apparatus according to the second or third aspect, there are a plurality of regions of interest as the region of interest.

According to a fifth aspect, in the X-ray CT apparatus according to the fourth aspect, the plurality of regions of interest are regions of interest in a plurality of images in different positions in a range of shuttle of the helical scan.

According to a sixth aspect, in the X-ray CT apparatus according to the fourth aspect, at least one of the plurality of regions of interest is a region of interest in which a change in a CT number is the maximum in an artery phase.

According to a seventh aspect, in the X-ray CT apparatus according to the fourth aspect, at least one of the plurality of regions of interest is a region of interest in which a change in a CT number is the maximum in a portal phase.

According to an eighth aspect, in the X-ray CT apparatus according to the fourth aspect, at least one of the plurality of regions of interest is a region of interest in which a change in a CT number is the maximum in a venous phase.

According to a ninth aspect, in the X-ray CT apparatus according to any one of the first to eighth aspects, the scan device performs a helical scan using the X-ray of the second X-ray dose at a preset timing.

According to a tenth aspect, in the X-ray CT apparatus according to the ninth aspect, the timing is set on the basis of a time density curve of the CT number in a region of interest in an image obtained by the contrast imaging by a pre-scan.

According to an eleventh aspect, there is provided a scan control method for an X-ray CT apparatus for performing contrast imaging by repetition of a helical shuttle scan on the same region in a subject, comprising a step of, repeating a helical shuttle scan including a helical scan using an X-ray of a first X-ray dose and a helical scan using an X-ray of a second X-ray dose higher than the first X-ray dose.

According to a twelfth aspect, in the scan control method according to the eleventh aspect, a start timing of the helical scan using the X-ray of the second X-ray dose is determined on the basis of a change in a CT number of a region of interest in an image captured by the helical scan using the X-ray of the first X-ray dose.

According to a thirteenth aspect, in the scan control method according to the eleventh or twelfth aspect, wherein said step of repeating a helical shuttle scan is performed by setting the first X-ray dose and the second X-ray dose for each of one way of paths of the helical shuttle scan.

According to a fourteenth aspect, in the scan control method according to the twelfth or thirteenth aspect, there are a plurality of regions of interest as the region of interest.

According to a fifteenth aspect, in the scan control method according to the fourteenth aspect, the plurality of regions of interest are regions of interest in a plurality of images in different positions in a range of shuttle of the helical scan.

According to a sixteenth aspect, in the scan control method according to the fourteenth aspect, at least one of the plurality of regions of interest is a region of interest in which a change in a CT number is the maximum in an artery phase.

According to a seventeenth aspect, in the scan control method according to the fourteenth aspect, at least one of the plurality of regions of interest is a region of interest in which a change in a CT number is the maximum in a portal phase.

According to an eighteenth aspect, in the scan control method according to the fourteenth aspect, at least one of the plurality of regions of interest is a region of interest in which a change in a CT number is the maximum in a venous phase.

According to a nineteenth aspect, in the scan control method according to any one of the eleventh to eighteenth aspects aspect, wherein said step of repeating a helical shuttle scan includes performing a helical scan using the X-ray of the second X-ray dose at a preset timing.

According to a twentieth aspect, in the scan control method according to the nineteenth aspect, the timing is set on the basis of a time density curve of the CT number in a region of interest in an image obtained by the contrast imaging by a pre-scan.

According to the first aspect, the X-ray CT apparatus for performing contrast imaging by repetition of a helical shuttle scan on the same region in a subject includes the scan device for repeating a helical shuttle scan including a helical scan using an X-ray of a first X-ray dose and a helical scan using an X-ray of a second X-ray dose higher than the first X-ray dose. Thus, the X-ray CT apparatus performing the contrast imaging by a helical shuttle scan with a reduced exposure amount can be realized.

According to the eleventh aspect, the scan control method for an X-ray CT apparatus for performing contrast imaging by repetition of a helical shuttle scan on the same region in a subject repeats a helical shuttle scan including a helical scan using an X-ray of a first X-ray dose and a helical scan using an X-ray of a second X-ray dose higher than the first X-ray dose. Thus, the scan control method of performing the contrast imaging by a helical shuttle scan with a reduced exposure amount can be realized.

In the second or twelfth aspect, a start timing of the helical scan using the X-ray of the second X-ray dose is determined on the basis of a change in a CT number of a region of interest in an image captured by the helical scan using the X-ray of the first X-ray dose. Thus, the helical scan using an X-ray of high dose can be performed at a proper timing.

In the third or thirteenth aspect, the first X-ray dose and the second X-ray dose are set for each of one way of paths of the helical shuttle scan, and the helical shuttle scan is repeated. Thus, the helical scan in which the X-ray dose in an ongoing path and that in a return path are different from each other can be performed.

According to the fourth or fourteenth aspect, there are a plurality of regions of interest as the region of interest. Thus, a plurality of timings for the helical scan using an X-ray of high dose can be determined.

According to the fifth or fifteenth aspect, the plurality of regions of interest are regions of interest in a plurality of images in different positions in a range of shuttle of the helical scan. Thus, the position of the region of interest can be optimized in the shuttle range of the helical scan.

According to the sixth or sixteenth aspect, at least one of the plurality of regions of interest is a region of interest in which a change in a CT number is the maximum in an artery phase. Consequently, an artery phase can be imaged by the helical scan using the X-ray of high dose.

According to the seventh or seventeenth aspect, at least one of the plurality of regions of interest is a region of interest in which a change in a CT number is the maximum in a portal phase. Consequently, a portal phase can be imaged by the helical scan using the X-ray of high dose.

According to the eighth or eighteenth aspect, at least one of the plurality of regions of interest is a region of interest in which a change in a CT number is the maximum in a venous phase. Consequently, a venous phase can be imaged by the helical scan using the X-ray of high dose.

According to the ninth or nineteenth aspect, the helical scan using the X-ray of the second X-ray dose is performed at a preset timing. Thus, it makes unnecessary to perform a data process during a low-dose scan, for determining the timing of a high-dose scan.

According to the tenth or twentieth aspect, the timing is set on the basis of a time density curve of the CT number in a region of interest in an image obtained by the contrast imaging by a pre-scan. Thus, the timing adapted to a blood flow state can be set.

DETAILED DESCRIPTION OF THE INVENTION

Figure 1:
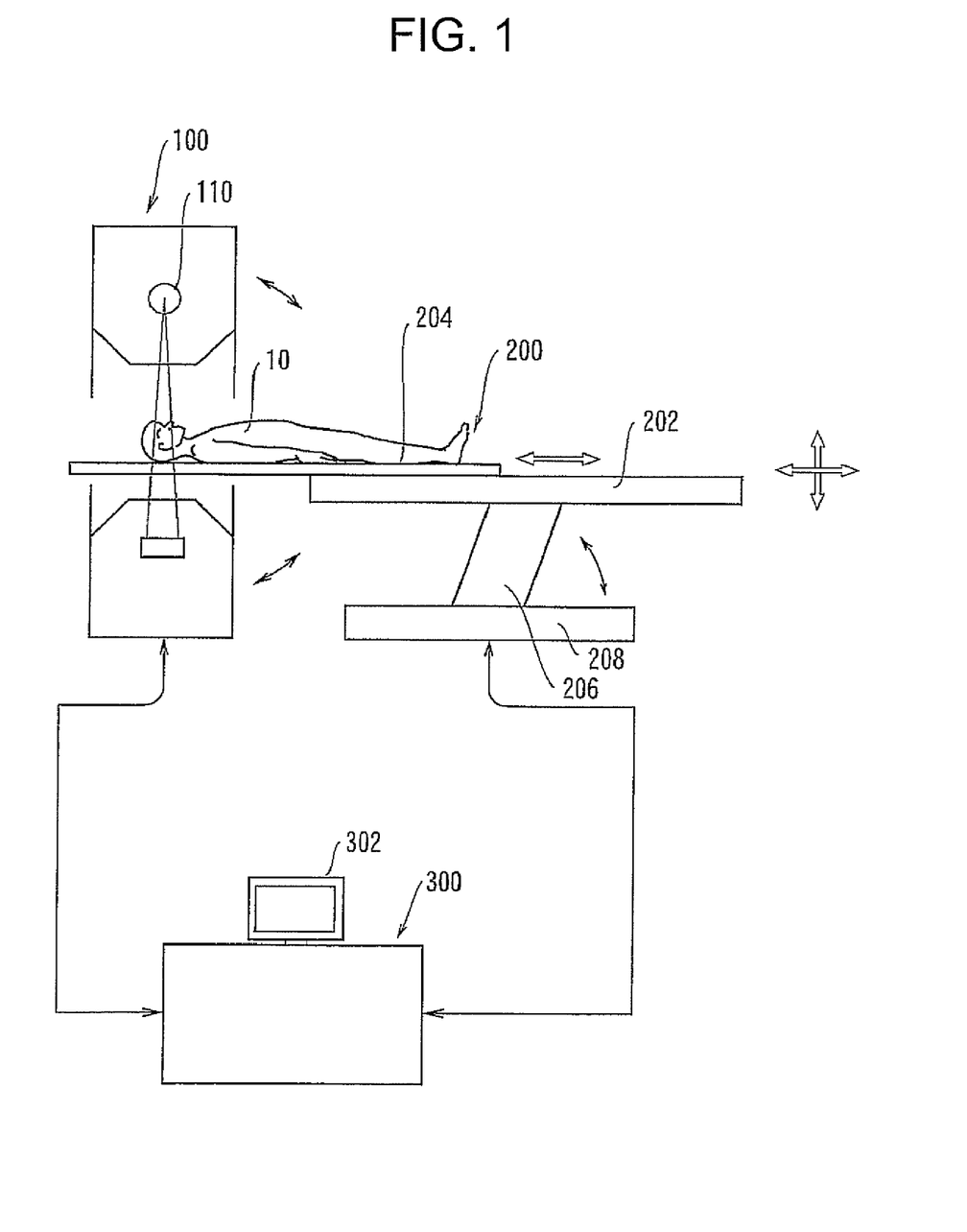
FIG. 1 is a diagram showing the configuration of an exemplary X-ray CT apparatus.

Embodiments of the invention will be described hereinbelow with reference to the drawings. The present invention is not limited to the embodiments described herein. FIG. 1 shows a schematic configuration of an X-ray CT apparatus.

The apparatus has a gantry 100, a table 200, and an operator console 300. The gantry 100 scans a subject 10 loaded on a table 200 with an X-ray irradiating/detecting apparatus 110 to collect projection data of a plurality of views, and inputs the collected projection data to the operator console 300. A part constructed by the gantry 100 and the table 200 is an example of scan device in the present invention.

The operator console 300 reconstructs an image on the basis of the projection data input from the gantry 100, and displays the reconstructed image on a display 302. The image reconstruction is performed by a dedicated computer in the operator 300.

The operator console 300 also controls the operation of the gantry 100 and the table 200. The control is performed by a dedicated computer in the operator 300. Under control of the operator console 300, the gantry 100 performs a scan with predetermined scanning parameters, and the table 200 positions the subject 10 so that a predetermined region is scanned. The positioning is performed by adjusting the height of a top board 202 and horizontal movement distance of a cradle 204 by a built-in position adjusting mechanism.

By performing a scan in a state where the cradle 204 is stopped, an axial scan can be performed. By performing the axial scan continuously for predetermined time, a cine scan can be conducted.

By continuously performing a scan a plurality of times while continuously moving the cradle 204, a helical scan can be performed. By continuously moving the cradle 204 so as to reciprocate during the helical scan, a reciprocal helical scan, that is, a helical shuttle scan can be performed.

The height of the top board 202 is adjusted by making a support 206 swing around the attachment part to a base 208 as a center. By the swing of the support 206, the top board 202 is displaced in the vertical and horizontal directions. The cradle 204 moves in the horizontal direction on the top board 202 to cancel out the displacement in the horizontal direction of the top board 202. Depending on a scan parameter, a scan is performed in a state where the gantry 100 is tilted. The gantry 100 is tilted by a built-in tilting mechanism.

Figure 2:
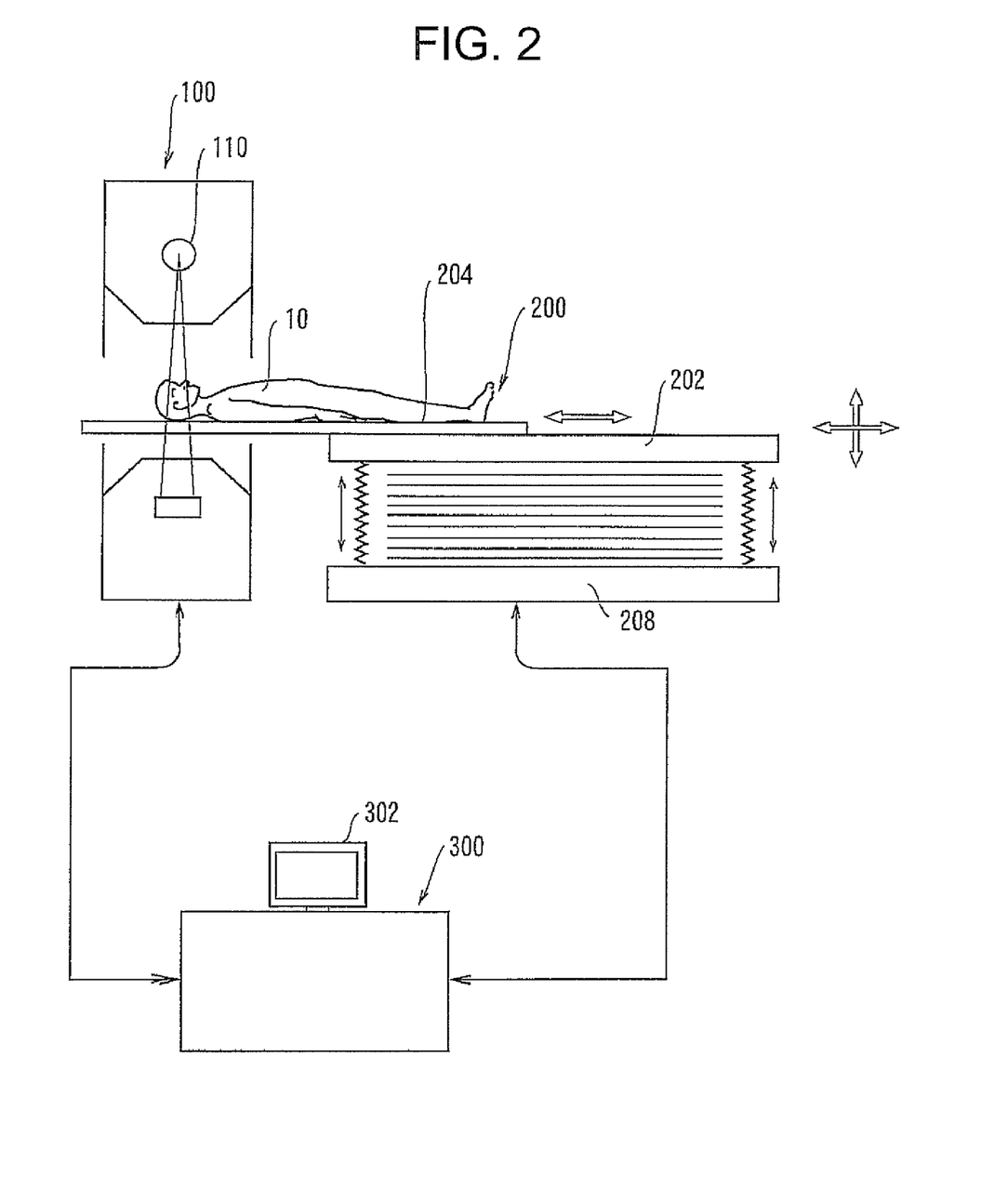
FIG. 2 is a diagram showing the configuration of a second embodiment of an X-ray CT apparatus.

As shown in FIG. 2, the table 200 may be of a type that the top board 202 elevates perpendicular to the base 208. The top board 202 is elevated by a built-in elevating, mechanism. In the table 200, horizontal movement of the top board 202 accompanying elevation does not occur.

Figure 3:
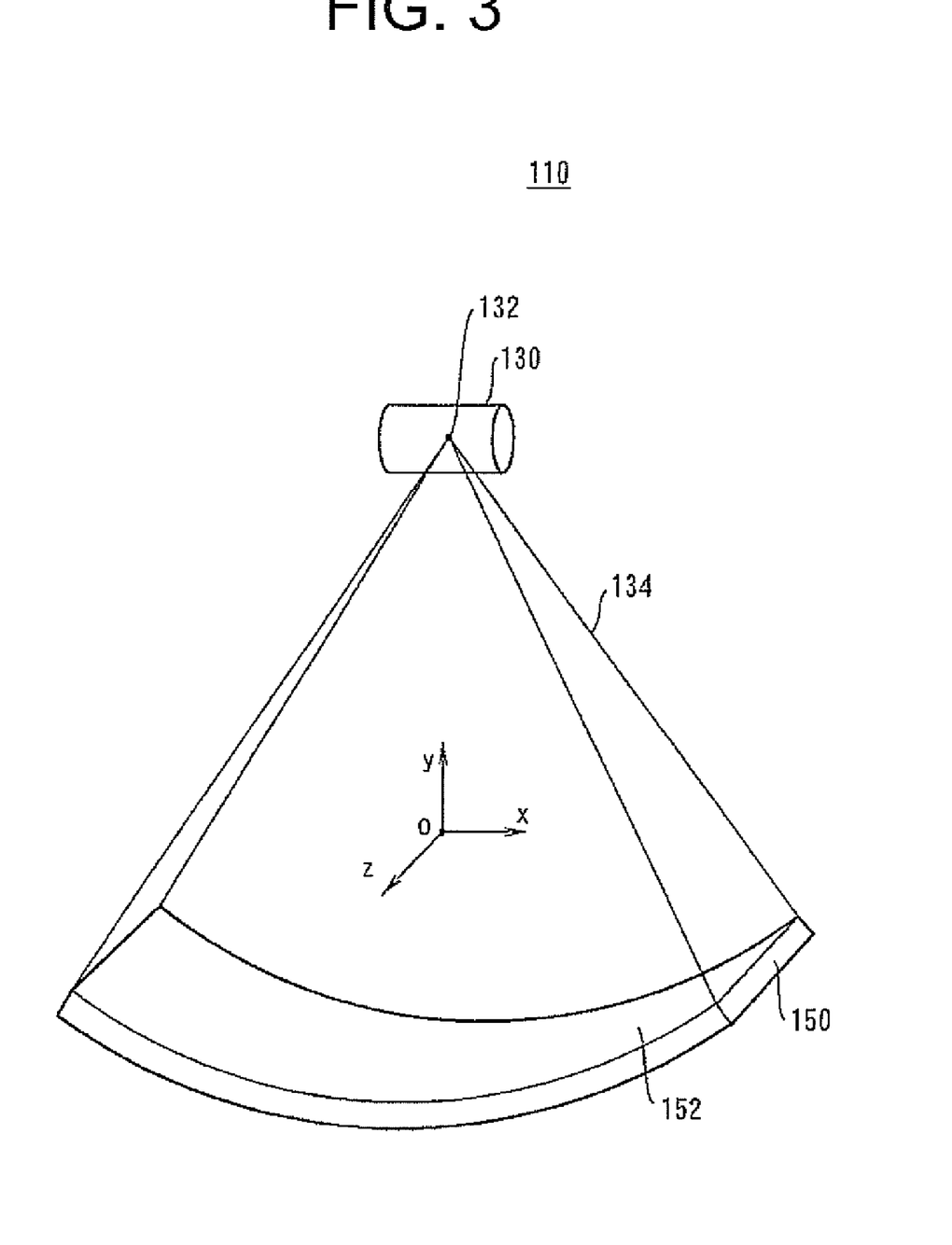
FIG. 3 is a diagram showing an exemplary configuration of an exemplary X-ray irradiating/detecting apparatus that may be used with the X-ray CT apparatus shown in FIGS. 1 and 2.

FIG. 3 schematically shows the configuration of the X-ray irradiating/detecting apparatus 110. The X-ray irradiating/detecting apparatus 110 detects an X-ray 134 emitted from a focal point 132 of an X-ray tube 130 by an X-ray detector 150.

The X-ray 134 is shaped by a not shown collimator to become an X-ray of a cone beam or fan beam. The X-ray detector 150 has an X-ray entrance plane 152 expanding two-dimensionally in correspondence with expansion of the X-ray. The X-ray entrance plane 152 is curved so as to construct a part of a cylinder. The center axis of the cylinder passes through the focal point 132.

The X-ray irradiating/detecting apparatus 110 rotates around the central axis passing through the image acquisition center, that is, isocenter O as a center. The central axis is parallel with the central axis of a partial cylinder formed by the X-ray detector 150.

The direction of the central axis of rotation is set as a z direction, the direction connecting the isocenter O and the focal point 132 is set as a z direction, and the direction perpendicular to the z and y directions is set as an x direction. The x-, y-, and z-axes are three axes of the rotating coordinate system using the z axis as a central axis.

Figure 4:
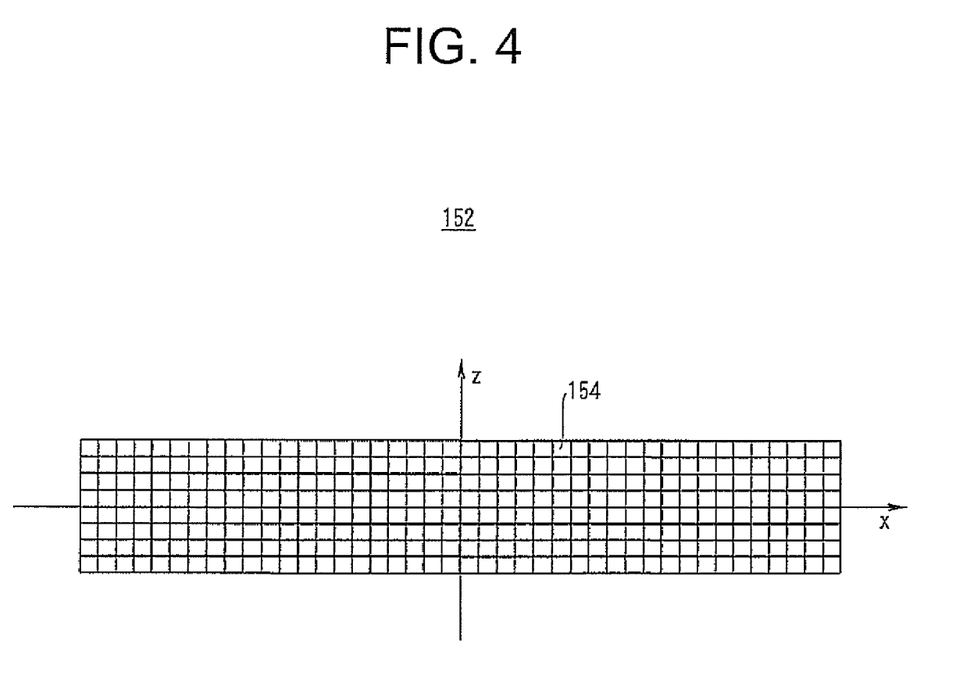
FIG. 4 is a diagram showing an exemplary configuration of an X-ray entrance plane of an X-ray detector that may be used with the X-ray irradiating/detecting apparatus shown in FIG. 3.

FIG. 4 is a schematic plan view of the X-ray entrance plane 152. In the X-ray entrance plane 152, detection cells 154 are arranged two-dimensionally in the x direction and the z direction. The X-ray entrance plane 152 is a two-dimensional array of the detection cells 154. In the case of using a fan-beam X-ray, a one-dimensional array of the detection cells 154 may be used as the X-ray entrance plane 152.

Each of the detection cells 154 serves as a detection channel in the X-ray detector 150. The X-ray detector 150 is a multi-channel X-ray detector. The detection cell 154 is constructed by, for example, a combination of a scintillator and a photo diode.

Figure 5:
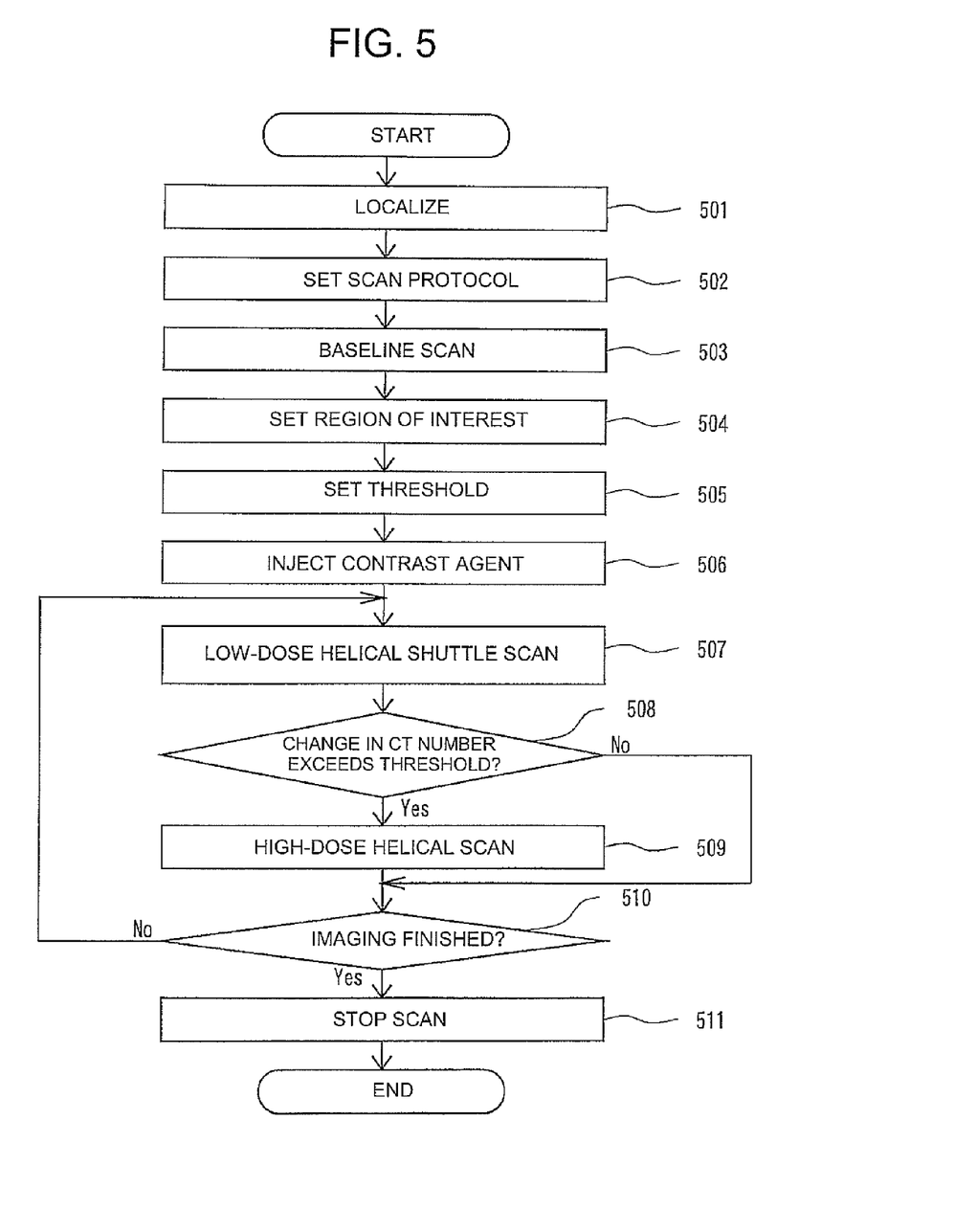
FIG. 5 is a flowchart showing an exemplary operation of the X-ray CT apparatus shown in FIGS. 1 and 2.

FIG. 5 shows a flowchart of an example of operation of the apparatus when contrast imaging is performed by a helical shuttle scan. The contrast imaging by the helical shuttle scan is performed under control of the operator console 300.

Figure 6:
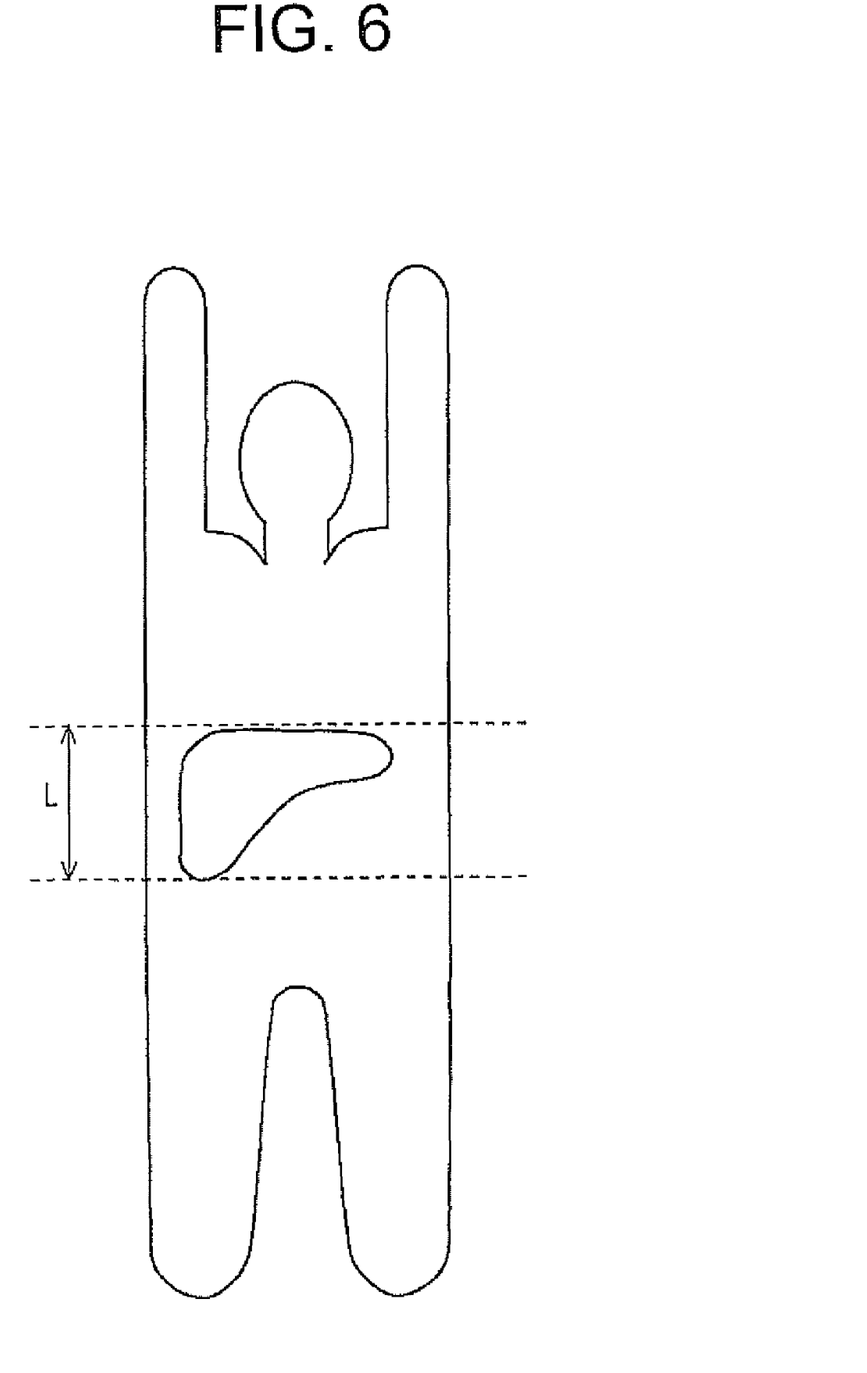
FIG. 6 is a diagram showing an example of setting of a scan range.

As shown in FIG. 5, localization is performed in step 501. The localization is performed by the operator through the operator console 300. By the operation, for example, as shown in FIG. 6, a scan range L including whole liver is set in the abdomen of the subject 10. The scan range is not limited to the abdomen but can be set in a desired region such as chest, head, or the like.

In step 502, a scan protocol is set. The scan protocol is set by the operator through the operator console 300. By the operation, required imaging parameters such as tube voltage and tube current of the X-ray tube, scan speed and duration of the helical shuttle scan, and image reconstruction parameters are set.

The tube current is set in two steps. One of the tube currents in two steps is set so that X-ray dose becomes a low dose (first X-ray dose). As such a current value, for example, 10 mA is set. The current value is much smaller than a current value of, for example, 300 mA or 500 mA commonly used in a conventional helical shuttle scan.

The other one of the tube currents in two steps is set so that the X-ray dose becomes a high dose (second X-ray dose). As such a current value, for example, 300 mA or 500 mA is set. The current value is similar to that commonly used in a conventional helical shuttle scan.

In step 503, a baseline scan is performed. The baseline scan is performed by helical-scanning the scan range 1 in a state where a contrast agent is injected.

By such a scan, images at positions in the scan range in a state where there is no contrast agent are acquired. The CT numbers of the images give a baseline for detecting a CT number change caused by the contrast agent.

Figures 7A, 7B, 7C:
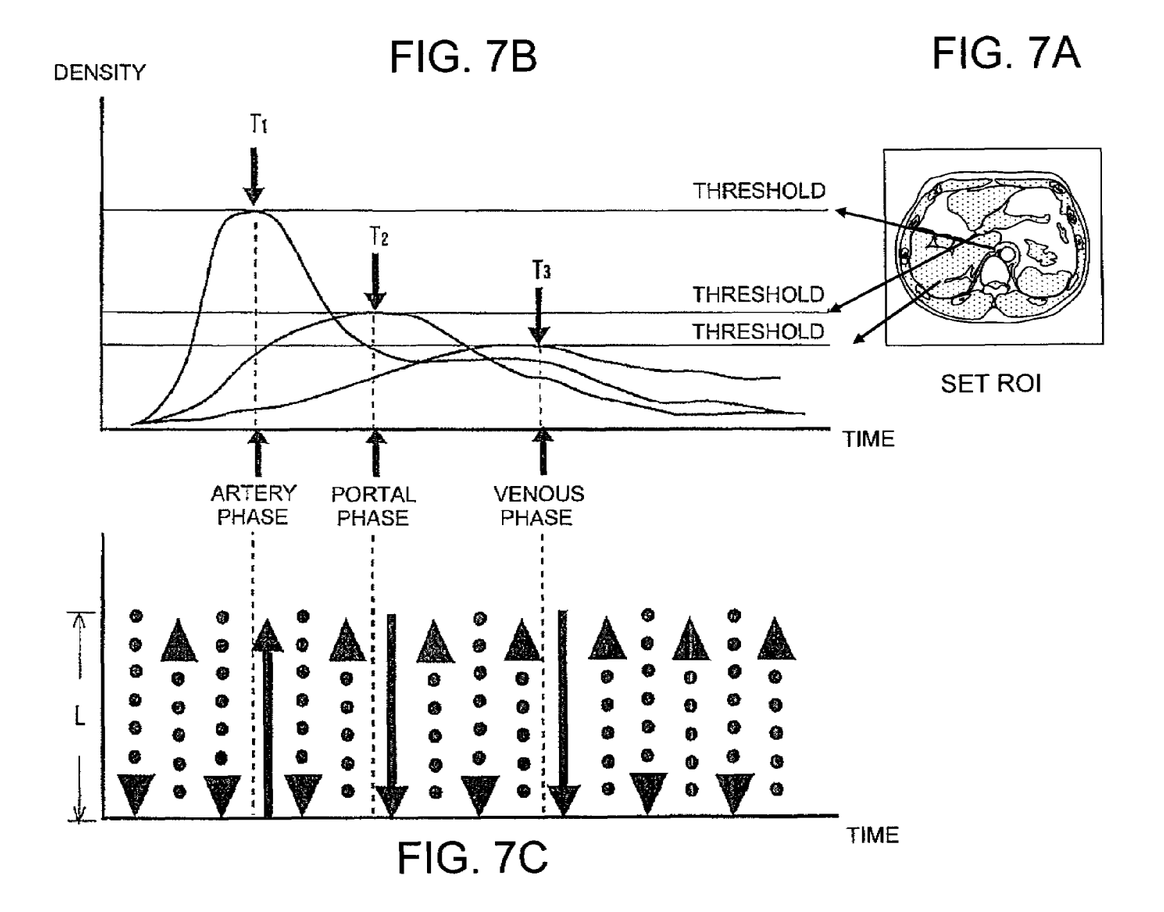
FIGS. 7(a), 7(b), and 7(c) are time charts showing the operation of the X-ray CT apparatus shown in FIGS. 1 and 2 using the operation shown in FIG. 5.

In step 504, a region of interest is set. The setting of a region of interest is performed by the operator through the operator console 300. The region of interest is set on an image. For example, as shown in FIG. 7A, the region of interest is set for each of an artery, a portal vein, and a vein.

In the following, the region of interest will be called ROI. An ROI set for an artery will be called an artery ROI, an ROI set for a portal vein will be called a portal ROI, and an ROI set for a vein will be called a venous ROI. The three ROIs can be set for separate images. In this case, images in which an artery, a portal vein, and a vein exist in a state optimal to the ROI setting are used.

In step 505, thresholds are set. The setting of a threshold is performed by the operator through the operator console 300. The threshold is a threshold related to a change amount of the CT number accompanying passage of a contrast agent. For example, as shown in FIG. 7B, a threshold is set for each ROI in accordance with a time density curve (TDC) of the ROI. The threshold set for the artery ROI is the largest, the threshold set for the portal ROI is the next largest, and the threshold set for the venous ROI is the smallest.

In step 506, a contrast agent is injected. Injection of a contrast medium is performed by intravenous injection by a not-shown dedicated injector or the like. By the operation, a predetermined amount of the contrast agent is injected into the subject 10. As the contrast agent, for example, iodine or the like is used.

In step 507, a low-dose helical shuttle scan is performed. The low-dose helical shuttle scan is a helical shuttle scan with an X-ray of the first X-ray dose. For example, it is a helical shuttle scan using 10 mA as a tube current.

By the helical shuttle scan, a real-time image is obtained in each of the positions in the scan range L. The CT number of the ROI of a real-time image increases as the contrast agent flows in, and decreases as the contrast agent flows out. Consequently, the change in the CT number from the baseline draws the time density curve.

In step 508, whether the change in the CT number of the ROI exceeds the threshold or not is determined. The determination is made on the basis of the thresholds of the three ROIs. When it is determined NO for all of the ROIs, whether imaging is finished or not is determined in step 510. The end of imaging is determined on the basis of, for example, whether scan duration has reached predetermined time or not.

When NO in step 510, the apparatus returns to step 507. While it is determined NO in the steps 508 and 510, the operations in the steps 507, 508, and 510 are repeated, and the low-dose helical shuttle scan is repeated.

In FIG. 7C, the low-dose helical shuttle scan is shown by a broken-line arrow. One arrow expresses a stroke of one way of the helical shuttle scan. The direction of the arrow expresses the travel direction of the helical shuttle scan. The length of the arrow expresses the scan range L.

When a change in the CT number of the artery ROI exceeds the threshold at time T1 during such a scan, on the basis of the determination in step 508, a high-dose helical scan is performed in step 509. The high-dose helical scan is a helical scan with an X-ray of the second X-ray dose higher than the first X-ray dose. For example, it is a helical scan using 500 mA as a tube current. The high-dose helical scan is expressed by a solid-line arrow in FIG. 7C.

The high-dose helical scan is performed in an entire going path or an entire return path in the scan range L. When the low-dose helical shuttle scan is on the going path at the time point when the change in the CT number of the artery ROI exceeds the threshold, the high-dose helical scan is performed in the return path. When the low-dose helical shuttle scan is on the return path, the high-dose helical scan is performed in the next going path.

By the high-dose helical scan, images of the arterial phase at positions in the scan range are obtained. Since the images of the arterial phase are acquired with the high-dose helical scan, the S/N ratio (signal-to-noise ratio) is high.

After the high-dose helical scan, whether the imaging is finished or not is determined in step 510. When NO in step 510, the apparatus returns to step 507. Consequently, the low-dose helical shuttle scan is restarted. While it is determined NO in the steps 508 and 510, the operations in the steps 507, 508, and 510 are repeated, and the low-dose helical shuttle scan is repeated. This state is expressed by two broken-line arrows after the solid-line arrow in FIG. 7C.

During such a scan, when the change in the CT number of the portal ROI exceeds the threshold at time T2, on the basis of the determination in step 508, a high-dose helical scan is performed in step 509. The high-dose helical scan is performed in an entire going path or an entire return path in the scan range L. In FIG. 7C, this state is expressed by the second solid-line arrow. By the operation, images of the portal phase at positions in the scan range L, are obtained. Since the images of the portal phase are acquired with the high-dose helical scan, the S/N ratio is high.

After the high-dose helical scan, whether the imaging is finished or not is determined in step 510. When NO in step 510, the apparatus returns to step 507. Consequently, the low-dose helical shuttle scan is restarted. While it is determined NO in the steps 508 and 510, the operations in the steps 507, 508, and 510 are repeated, and the low-dose helical shuttle scan is repeated. This state is expressed by three broken-line arrows after the solid-line arrow in FIG. 7C.

During such a scan, when the change in the CT number of the venous ROI exceeds the threshold at time T3, on the basis of the determination in step 508, a high-dose helical scan is performed in step 509. In FIG. 7C, this state is expressed by the third solid-line arrow. By the operation, images of the venous phase at positions in the scan range L are obtained. Since the images of the venous phase are acquired with the high-dose helical scan, the S/N ratio is high.

After the high-dose helical scan, whether the imaging is finished or not is determined in step 510. When NO in step 510, the apparatus returns to step 507. Consequently, the low-dose helical shuttle scan is restarted. While it is determined NO in the steps 508 and 510, the operations in the steps 507, 508, and 510 are repeated, and the low-dose helical shuttle scan is repeated. This state is expressed by five broken-line arrows after the solid-line arrow in FIG. 7C.

After that, when the scan duration reaches predetermined time time, it is determined in step 510 that the imaging is finished, and the scan is stopped in step 511.

As described above, in the helical shuttle scan for contrast imaging, a scan for monitoring a change in the CT number of the ROI is performed with a low dose. Only a scan for capturing a contrast image of each phase is performed with a high dose. The proportion occupying the scan duration, of the low-dose helical shuttle scan is overwhelming and that of the high-dose helical scan is a little.

Consequently, as compared with the conventional case of performing a scan with the high dose, the exposure dose of the subject can be largely reduced. On the other hand, contrast images of the phases are acquired with the high-dose scan, so that contrast images of high quality and high S/N ratio can be obtained.

Figure 8:
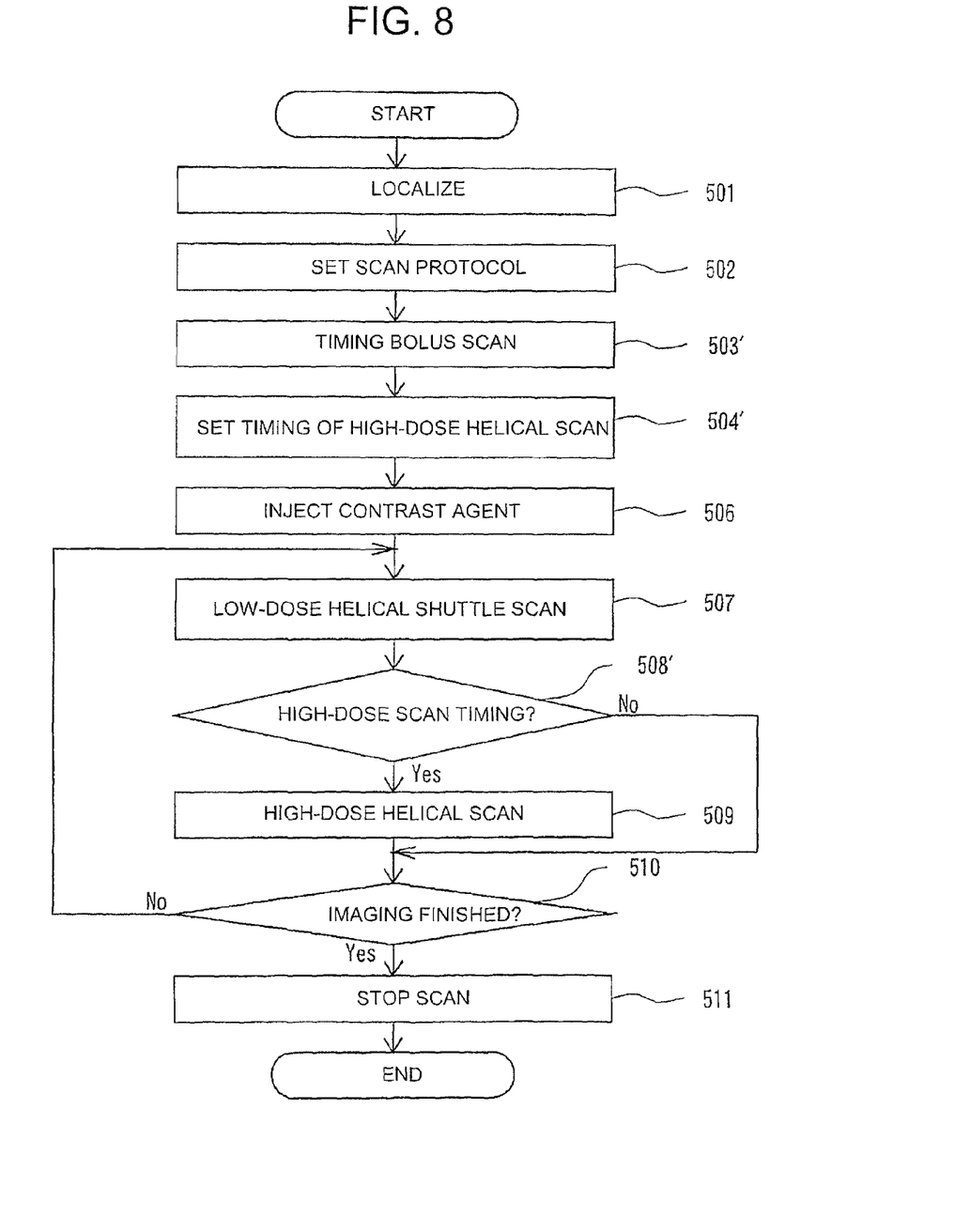
FIG. 8 is a flowchart showing another exemplary operation of the X-ray CT apparatus shown in FIGS. 1 and 2.

FIG. 8 is a flowchart showing another example of the operation of the apparatus at the time of performing contrast imaging by the helical shuttle scan. The contrast imaging by the helical shuttle scan is performed under control of the operator console 300.

In FIG. 8, the same numbers are designated to steps similar to those of FIG. 5 and the description will not be repeated. A first point different from FIG. 5 is that a timing bolus scan is performed in step 503'. By the timing bolus scan, a small amount of the contrast agent is injected to the subject 10, a predetermined section is repeatedly scanned with a low dose, and the time density curve of an artery is obtained. The timing bolus scan is an example of a pre-scan in the present invention.

A second point different from FIG. 5 is that the start timing of the high-dose helical scan is set in step 504'. The start timing of the high-dose helical scan is set by predicting, for example, early artery phase, late artery phase, portal phase, and venous phase from the time density curve obtained as described above. In such a manner, the timing adapted to a blood flow state can be set.

For prediction of the phases, a predetermined algorithm is used. The timings which are set are, for example, time A adapted to the early artery phase, time B adapted to the late artery phase, time C adapted to the portal phase, and time D adapted to the venous phase.

Figure 9:
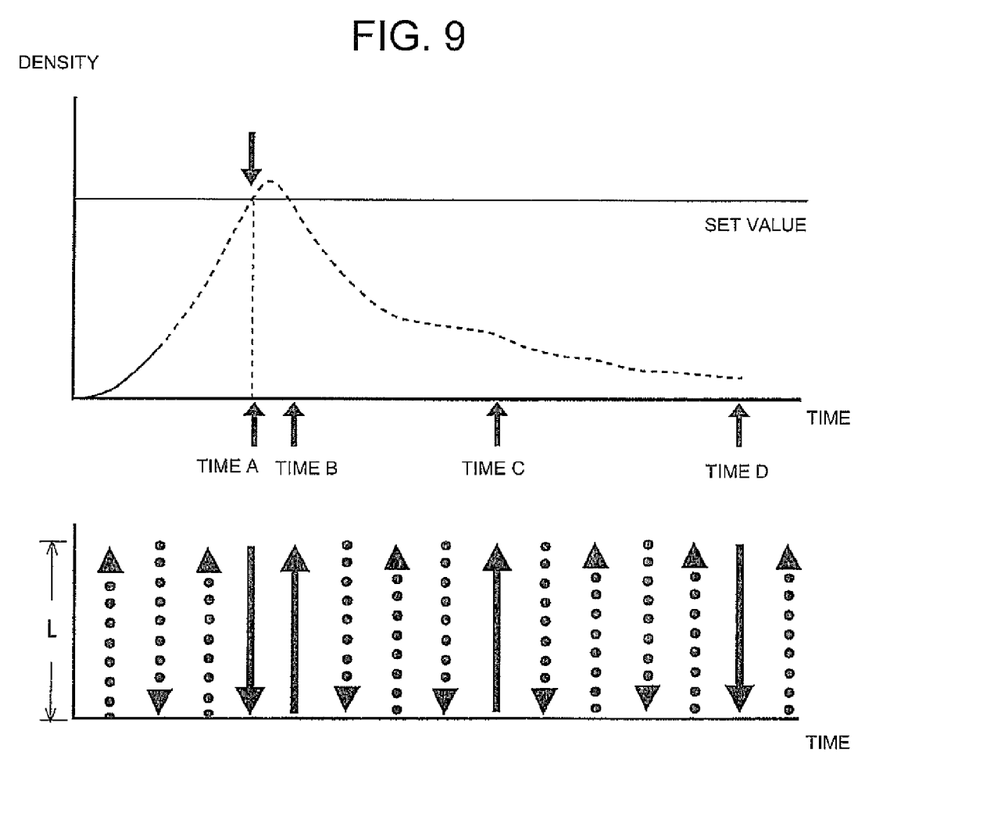
FIG. 9 is a time chart showing the operation of the X-ray CT apparatus shown in FIGS. 1 and 2 using the operation shown in FIG. 8.

A third point different from FIG. 5 is that there is no threshold setting corresponding to step 505. A fourth point different from FIG. 5 is that the start timing of the high-dose helical scan is determined in step 508'. On the basis of the determination, as shown in FIG. 9, the high-dose helical scan is performed at each of the time A, B, C, and D. At the other timings, the low-dose helical scan is performed. The time A is expected time at which the CT number change of the artery exceeds the set value.

As described above, the helical scan with a high-dose X-ray is performed at a preset timing. It makes unnecessary to perform reconstruction of a real-time image and monitoring of the CT number of an ROI during the low-dose scan for determining the timing of the high-dose.

Figure 10:
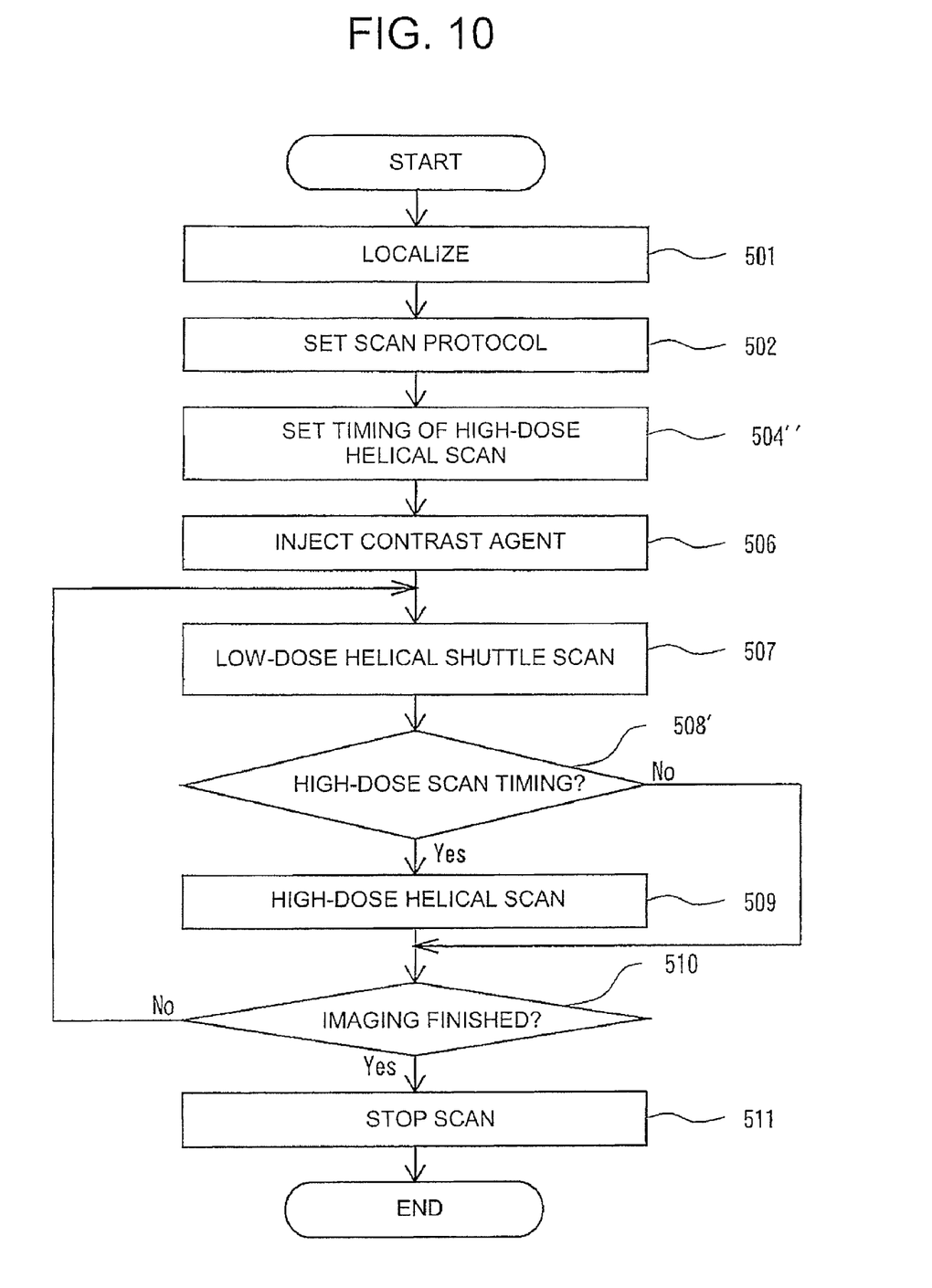
FIG. 10 is a flowchart showing a third exemplary operation of the X-ray CT apparatus shown in FIGS. 1 and 2.

FIG. 10 is a flowchart showing further another example of the operation of the apparatus at the time of performing contrast imaging using a helical shuttle scan. The contrast imaging using a helical shuttle scan is performed under control of the operator console 300.

In FIG. 10, the same numbers are designated to steps similar to those of FIG. 8 and the description will not be repeated. A point different from FIG. 8 is that the timing bolus scan in step 503' is not performed. In step 504", a start timing of the high-dose helical scan is set.

The start timing of the high-dose helical scan is manually set by predicting, for example, early artery phase, late artery phase, portal phase, and venous phase. For prediction of the phases, actual data of contrast imaging in the past and the like is used.

The timings which are set are, for example, time A adapted to the early artery phase, time B adapted to the late artery phase, time C adapted to the portal phase, and time D adapted to the venous phase. The timings are not limited to those timings. An arbitrary timing can be set as the start timing of the high-dose helical scan.

On the basis of such setting, in a manner similar to FIG. 9, the high-dose helical scan is performed at each of the time A, B, C, and D. At the other timings, the low-dose helical scan is performed.

When the start timings A, B, C, and D of the high-dose helical scan are preliminarily determined, steps in the low-dose helical shuttle scan, in which the timings fall can be predicted.

When it is expected that the start timing of the high-dose helical scan arrives in a going path or a return path in the low-dose helical shuttle scan, the process can be performed by the high-dose helical scan in place of the low-dose helical shuttle scan.

What is claimed is:

1. An X-ray computed tomography (CT) apparatus for performing contrast imaging by performance of a helical shuttle scan on a region of interest in a subject, said X-ray CT apparatus comprising:
    a scan device configured to set a plurality of X-ray doses and perform a helical shuttle scan, said helical shuttle scan comprising:
        a plurality of helical scan paths, each helical scan path at least partially defined by travel of a region of interest along a predetermined distance along a one-way travel stroke; and
        a first helical scan of said region of interest emitting an X-ray of a first X-ray dose and a second helical scan of said region of interest emitting an X-ray of a second X-ray dose, said second X-ray dose greater than said first X-ray dose, said first helical scan performed along at least one of said plurality of helical scan paths until a predetermined threshold value of change of CT numbers is exceeded while said region of interest travels along a first one-way travel stroke, said second helical scan comprising a single helical scan performed immediately and automatically thereafter, wherein said region of interest travels along a second one-way travel stroke opposite to the first one-way travel stroke; and
    an image reconstruction device configured to reconstruct images corresponding to each of said plurality of helical scan paths.

2. The X-ray CT apparatus according to claim 1, wherein said region of interest comprises a plurality of regions of interest.

3. The X-ray CT apparatus according to claim 2, wherein said plurality of regions of interest are regions of interest in a plurality of images in different positions in a range of shuttle of said helical shuttle scan.

4. The X-ray CT apparatus according to claim 2, wherein at least one of said plurality of regions of interest is a region of interest in which a change in a CT number is a maximum value in an artery phase.

5. The X-ray CT apparatus according to claim 2, wherein at least one of said plurality of regions of interest is a region of interest in which a change in a CT number is a maximum value in a portal phase.

6. The X-ray CT apparatus according to claim 2, wherein at least one of said plurality of regions of interest is a region of interest in which a change in a CT number is a maximum value in a venous phase.

7. The X-ray CT apparatus according to claim 1, wherein said scan device is configured to perform said second helical scan using the X-ray of said second X-ray dose at a preset timing.

8. The X-ray CT apparatus according to claim 7, wherein the timing is set on the basis of a time density curve of a CT number in a region of interest in an image obtained by the contrast imaging by a pre-scan.

9. A method for controlling an X-ray computed tomography (CT) apparatus for performing contrast imaging during a helical shuttle scan on a region of interest in a subject, said method comprising:
    defining a plurality of helical scan paths, each helical scan path at least partially defined by travel of the region of interest along a predetermined distance along a one-way travel stroke;
    setting a first X-ray dose and a second X-ray dose, the second X-ray dose is greater than the first X-ray dose;
    performing a helical shuttle scan comprising:
        performing at least one first helical scan of the region of interest emitting an X-ray of the first X-ray dose along at least one of the plurality of helical scan paths;
        exceeding a predetermined threshold value of change of CT numbers while the region of interest travels along a first one-way travel stroke; and
        immediately and automatically performing a single second helical scan emitting an X-ray of the second X-ray dose while the region of interest travels along a second one-way travel stroke opposite to the first one-way travel stroke; and
    reconstructing images corresponding to each of the at least one first helical scan and the single second helical scan.

10. The method according to claim 9, wherein there are a plurality of regions of interest as the region of interest.

11. The method according to claim 10, wherein the plurality of regions of interest are regions of interest in a plurality of images in different positions in a range of shuttle of the helical shuttle scan.

12. The method according to claim 10, wherein at least one of the plurality of regions of interest is a region of interest in which a change in a CT number is a maximum value in an artery phase.

13. The method according to claim 10, wherein at least one of the plurality of regions of interest is a region of interest in which a change in a CT number is a maximum value in a portal phase.

14. The method according to claim 10, wherein at least one of the plurality of regions of interest is a region of interest in which a change in a CT number is a maximum value in a venous phase.

15. The method according to claim 9, wherein performing a helical shuttle scan further comprises performing a helical scan emitting the X-ray of the second X-ray dose at a preset timing.

16. The method according to claim 15 further comprising setting the timing based on a time density curve of a CT number in a region of interest in an image obtained by the contrast imaging by a pre-scan.

* * * * *